US011116454B2

(12) United States Patent
Ishikawa

(10) Patent No.: US 11,116,454 B2
(45) Date of Patent: Sep. 14, 2021

(54) IMAGING DEVICE AND METHOD

(71) Applicant: Shimadzu Corporation, Kyoto (JP)

(72) Inventor: Akihiro Ishikawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 511 days.

(21) Appl. No.: 16/039,536

(22) Filed: Jul. 19, 2018

(65) Prior Publication Data

US 2020/0022655 A1    Jan. 23, 2020

(51) Int. Cl.
*A61B 5/00* (2006.01)
*G06T 5/00* (2006.01)

(52) U.S. Cl.
CPC .......... *A61B 5/7214* (2013.01); *A61B 5/0071* (2013.01); *G06T 5/002* (2013.01); *G06T 2207/10064* (2013.01); *G06T 2207/30004* (2013.01)

(58) Field of Classification Search
CPC ..... A61B 5/7214; A61B 5/0071; G06T 5/002; G06T 2207/30004; G06T 2207/10064
See application file for complete search history.

(56) References Cited

U.S. PATENT DOCUMENTS

| | | | |
|---|---|---|---|
| 2008/0310721 A1* | 12/2008 | Yang | G06K 9/3275 382/182 |
| 2009/0285760 A1 | 11/2009 | Osamu et al. | |
| 2010/0056918 A1 | 3/2010 | Sato et al. | |
| 2015/0104396 A1 | 4/2015 | Osamu et al. | |
| 2016/0253800 A1* | 9/2016 | Gurevich | G06T 7/0016 382/128 |

FOREIGN PATENT DOCUMENTS

| | | |
|---|---|---|
| JP | H08-336508 A | 12/1996 |
| JP | 2008-301934 A | 12/2008 |
| JP | 2010-51729 A | 3/2010 |
| JP | 2011-509768 A | 3/2011 |
| WO | 2009/092162 A1 | 7/2009 |
| WO | 2009/139466 A | 11/2009 |

OTHER PUBLICATIONS

Office Action dated Oct. 9, 2018 in corresponding Japanese Application No. 2016-004114; 4 pages including English-language translation.

* cited by examiner

*Primary Examiner* — Bo Joseph Peng
(74) *Attorney, Agent, or Firm* — Maier & Maier, PLLC

(57) ABSTRACT

An imaging device and method which can easily obtain a curve of time-varying changes in pixel value of a region of interest, even if the region of interest moves with a subject's body motion. A controller includes an image processor executing various types of image processing on fluorescence images and visible light images. The image processor includes a pixel value measurement unit which sequentially measures values of pixels at positions corresponding to a region of interest (ROI) in the fluorescence image, a change curve creation unit which creates a curve of time-varying changes in pixel value of the ROI by sampling, among the pixel values measured by the pixel value measurement unit, a minimum pixel value within a period equal to or longer than a cycle of the subject's body motion, and a smoothing unit which smooths the curve created by the change curve creation unit.

2 Claims, 9 Drawing Sheets

IMAGING DEVICE AND METHOD

BACKGROUND

The present disclosure relates to an imaging device and method for irradiating a fluorescent dye administered in a body of a subject with excitation light, and taking an image of fluorescence emitted from the fluorescent dye.

A technique called "near-infrared fluorescence imaging" has been used for angiography in surgery. According to the near-infrared fluorescence imaging, indocyanine green (ICG), which is a fluorescent dye, is administered to an affected area using an injector or any other suitable means. Upon receipt of near-infrared light having a wavelength of about 600 to 850 nm as excitation light, indocyanine green emits near-infrared fluorescence having a wavelength of about 750 to 900 nm. An image of the fluorescence is captured by an image sensor capable of detecting the near-infrared light, and is shown on a display unit such as a liquid crystal display panel. According to the near-infrared fluorescence imaging, blood vessels and lymphatics at the depth of about 20 mm from the body surface can be observed.

Further, attention has recently been paid to a technique of fluorescence-labeling a tumor for the purpose of surgery navigation. As a fluorescent marker used for the fluorescence-labeling of the tumor, 5-aminolevulinic acid is used. When administered to a subject, 5-aminolevulinic acid (will be hereinafter abbreviated as "5-ALA") is metabolized by protoporphyrin IX (PpIX), which is one of the fluorescent dyes. PpIX specifically accumulates in cancer cells. When visible light having a wavelength of about 410 nm is applied to PpIX, which is a metabolite of 5-ALA, PpIX emits red visible light having a wavelength of about 630 nm as fluorescence. Thus, the cancer cells can be identified through the observation of the fluorescence from PpIX.

International Patent Publication No. 2009/139466 discloses a data collection method. In this method, an intensity distribution image of near-infrared fluorescence obtained through excitation light irradiation of a subject organ of a living body administered with indocyanine green is compared with a cancer lesion distribution image obtained through X-ray irradiation, nuclear magnetic resonance, or ultrasonography performed on the subject organ before the administration of indocyanine green. Then, data of a region which is detected in the intensity distribution image of the near-infrared fluorescence, but not in the cancer lesion distribution image is collected as data of a sub-lesion region of cancer.

In the imaging device configured to take an image of the fluorescence from the fluorescent dye injected in the body, the fluorescence from the subject and images of the subject under visible light are simultaneously recorded as a video, which is reproduced by a video recorder. Thus, according to a conventional imaging device, images taken at a predetermined frame rate are recorded and reproduced as a video, so that the courses of the blood vessels and the lymphatics after the administration of the fluorescent dye such as ICG can be observed, and a region of a cancer lesion can be identified, in a bright external lighting environment.

Such recorded data can be used not only for reference purposes, but also for obtaining new findings through analyses. For example, in a time intensity curve (TIC) analysis in which a curve of time-varying changes in signal of a region of interest (ROI) is created, time taken until the pixel value of the ROI reaches the peak is obtained so that imaging time of the fluorescent dye such as indocyanine green can be quantitatively evaluated. For example, it is advantageous to obtain a curve of time-varying changes in pixel value of the ROI for the confirmation of blood flow after coronary artery bypass graft surgery.

If a region accompanied by a body motion of a subject, such as heart, is selected as the ROI to be analyzed, correction taking the subject's body motion into account is required. For example, if cardiac muscle is selected as the ROI while cardiac vessels are moving with the pulsation during the analysis, the cardiac vessels may enter the region to be analyzed. As a result, periodical components of a cardiovascular region associated with the subject's body motion may be superimposed on the TIC.

Japanese Unexamined Patent Publication No. 2010-51729 discloses an ultrasonic diagnostic apparatus which corrects movements associated with a subject's body motion by vector calculation.

SUMMARY

For example, if a myocardial region is selected as the ROI of the TIC analysis, the cardiac vessels need to be fixed (locked). However, it is impossible to fix the whole blood vessels in every region for the vector calculation disclosed by Japanese Unexamined Patent Publication No. 2010-51729. Specifically, in the vector calculation disclosed by Japanese Unexamined Patent Publication No. 2010-51729, it takes a long time to perform the correction calculation involving spatial movement, and thus, it is impossible to fix the blood vessels in every region.

In view of the foregoing, the present disclosure has been achieved to provide an imaging device and method which can easily obtain a curve of time-varying changes in pixel value of a region of interest, even if the region of interest moves along with a body motion of a subject.

A first aspect of the present disclosure is directed to an imaging device which includes: an excitation light source which irradiates a subject with excitation light for exciting a fluorescent dye administered to the subject; a shooting unit which shoots fluorescence emitted from the fluorescent dye irradiated with the excitation light to obtain a fluorescence image; and an image storage which sequentially stores the fluorescence image that changes with a body motion of a subject. The imaging device further includes: a pixel value measurement unit which sequentially measures values of pixels at positions corresponding to a region of interest in the fluorescence image; and a change curve creation unit which creates a curve of time-varying changes in pixel value of the region of interest by sampling, among the pixel values measured by the pixel value measurement unit, a maximum pixel value within a period equal to or longer than a cycle of the subject's body motion.

A second aspect of the present disclosure is an embodiment of the first aspect. In the second aspect, the imaging device further includes a smoothing unit which smooths the curve created by the change curve creation unit.

A third aspect of the present disclosure is directed to an imaging method for sequentially obtaining a fluorescence image that changes with a body motion of a subject through irradiation of the subject with excitation light to excite a fluorescent dye administered to the subject, and shooting of fluorescence emitted from the fluorescent dye irradiated with the excitation light. The method includes: sequentially measuring values of pixels at positions corresponding to a region of interest in the fluorescence image; and creating a curve of time-varying changes in pixel value of the region of interest by sampling, among the pixel values measured by the pixel value measurement unit, a minimum pixel value within a period equal to or longer than a cycle of the subject's body motion.

A fourth aspect of the present disclosure is an embodiment of the third aspect. In the fourth aspect, the imaging method further includes smoothing the curve created by the change curve creation unit.

According to the first and third aspects of the present disclosure, a curve of time-varying changes in pixel value of a region of interest in a fluorescence image can easily be obtained, even if the region of interest moves along with a subject's body motion.

According to the second and fourth aspects of the present disclosure, a smoothed curve of time-varying changes in pixel value of a region of interest in a fluorescence image can be obtained.

DETAILED DESCRIPTION

Figure 1:
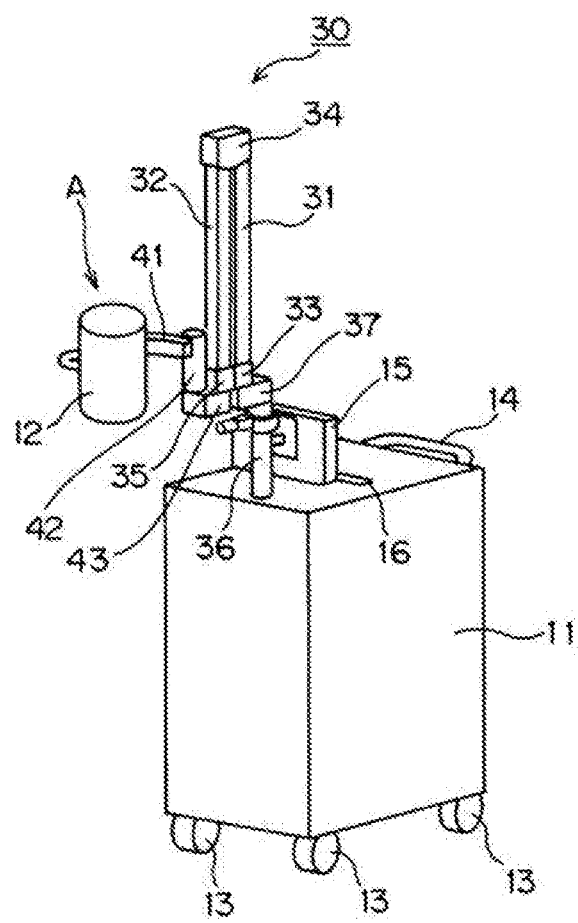
FIG. 1 is a perspective view illustrating an imaging device of the present disclosure.
Figure 2:
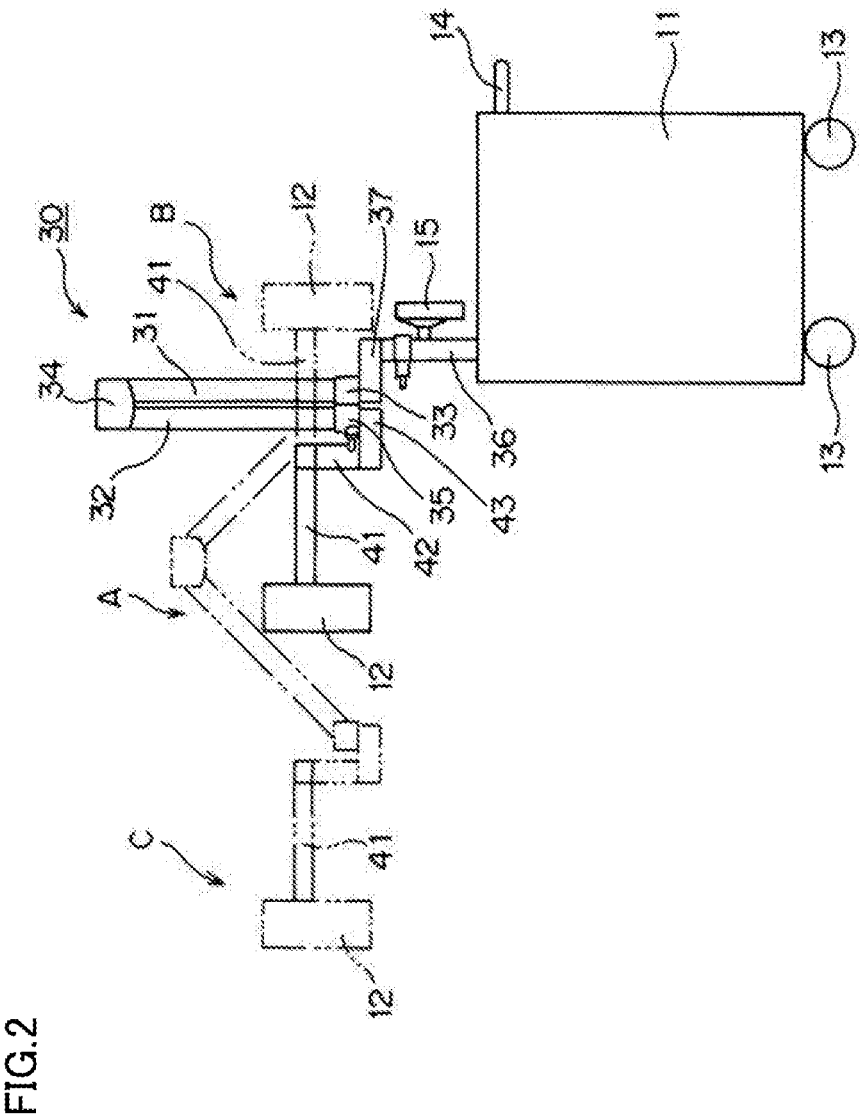
FIG. 2 is a side view illustrating the imaging device of the present disclosure.
Figure 3:
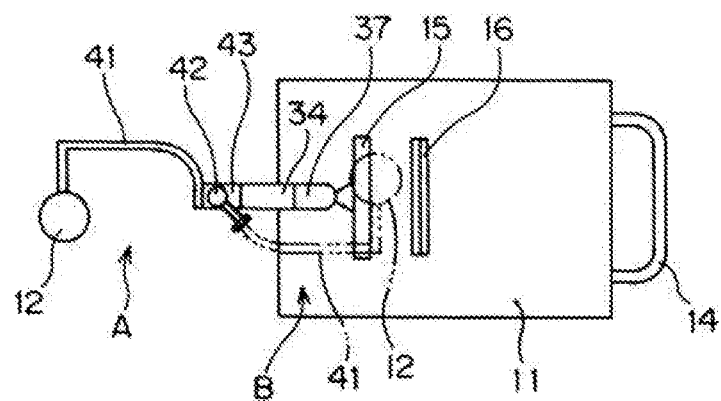
FIG. 3 is a plan view illustrating the imaging device of the present disclosure.

Embodiments of the present disclosure will be described in detail with reference to the drawings. FIG. 1 is a perspective view illustrating an imaging device of the present disclosure. FIG. 2 is a side view illustrating the imaging device of the present disclosure. FIG. 3 is a plan view illustrating the imaging device of the present disclosure.

The disclosed imaging device irradiates indocyanine green, which is a fluorescent dye injected into a body of a subject, with excitation light, and shoots fluorescence emitted from indocyanine green. The imaging device includes a wagon 11 with four wheels 13, an arm mechanism 30 disposed on a portion of a top surface of the wagon 11 toward the front in a traveling direction of the wagon 11 (toward the left in FIGS. 2 and 3), a lighting/shooting unit 12 provided for the arm mechanism 30 via a sub-arm 41, and a monitor 15. The "front in the traveling direction" of the wagon 11 will be hereinafter simply referred to as the "front" of the wagon 11. A handle 14 used to move the wagon 11 is attached to a rear side of the wagon 11 in the traveling direction. A recess 16 is formed at the top surface of the wagon 11 so that a remote control used to operate the imaging device from a distance can fit therein.

The arm mechanism 30 is disposed on the front portion of the wagon 11. The arm mechanism 30 includes a first arm member 31 which is coupled via a hinge 33 to a support 37 arranged on a column 36 standing upright on the front portion of the wagon 11. The first arm member 31 is able to swing with respect to the wagon 11 via the column 36 and the support 37 by the action of the hinge 33. The monitor 15 is attached to the column 36.

A second arm member 32 is coupled to an upper end of the first arm member 31 via a hinge 34. The second arm member 32 is able to swing with respect to the first arm member 31 by the action of the hinge 34. In this configuration, the first and second arm members 31 and 32 are able to take a shooting position as indicated by reference character C and phantom lines in FIG. 2, and a standby position as indicated by reference character A and solid lines in FIGS. 1 to 3. In the shooting position, the first and second arm members 31 and 32 form a predetermined angle around the hinge 34 coupling the first and second arm members 31 and 32. In the standby position, the first and second arm members 31 and 32 are adjacent to each other.

A support 43 is coupled to a lower end of the second arm member 32 via a hinge 35. The support 43 is able to swing with respect to the second arm member 32 by the action of the hinge 35. The support 43 supports a rotation axis 42. The sub-arm 41 supporting the lighting/shooting unit 12 rotates about the rotation axis 42 disposed at a tip end of the second arm member 32. Thus, through the rotation of the sub-arm 41, the lighting/shooting unit 12 moves between a front position and a rear position with respect to the arm mechanism 30 in the traveling direction of the wagon 11. The front position, which corresponds to the shooting position or the standby position, is indicated by reference character A and solid lines in FIGS. 1 to 3, or reference character C and phantom lines in FIG. 2. The rear position, which is a position during the movement of the wagon 11, is indicated by reference character B and phantom lines in FIGS. 2 and 3.

Figure 4:
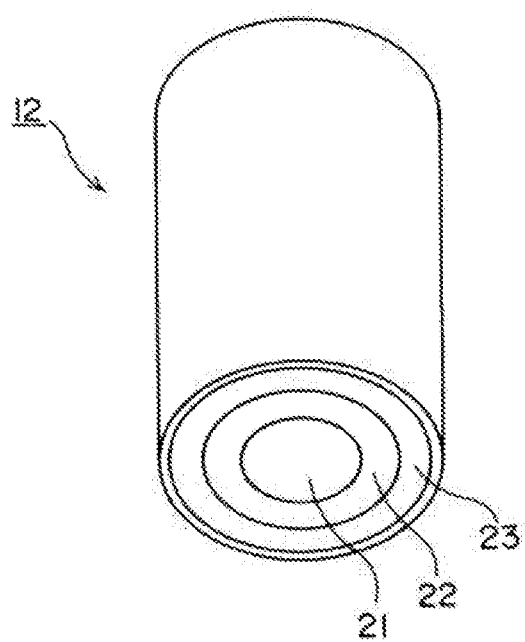
FIG. 4 is a schematic view of a lighting/shooting unit 12.

FIG. 4 schematically shows the lighting/shooting unit 12.

The lighting/shooting unit 12 includes a camera 21 including a plurality of image sensors capable of capturing visible light and near-infrared light, a visible light source 22 disposed on the outer periphery of the camera 21, and an excitation light source 23 disposed on the outer periphery of the visible light source 22. The visible light source 22 emits white light (visible light). The excitation light source 23 emits near-infrared light having a wavelength of 810 nm as excitation light for exciting indocyanine green which is a fluorescent dye. Indocyanine green emits, as fluorescence, near-infrared light having a peak around 845 nm when irradiated with the near-infrared light having a wavelength of 810 nm.

In this embodiment, the visible light source 22, the excitation light source 23, and the camera 21 are integrated into the lighting/shooting unit 12. Alternatively, the visible light source 22, the excitation light source 23, and the camera 21 may be separately arranged.

Figure 5:
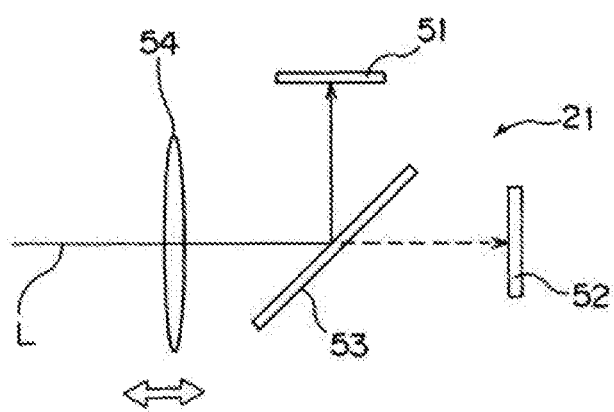
FIG. 5 is a schematic view of a camera 21 of the lighting/shooting unit 12.

FIG. 5 is a schematic view of the camera 21 of the lighting/shooting unit 12.

The camera 21 includes a moving lens 54 which reciprocates for focusing, a wavelength selection filter 53, a visible light image sensor 51, and a fluorescence image sensor 52. The visible light image sensor 51 and the fluorescence image sensor 52 are comprised of CMOS or CCDs. Visible light and fluorescence coaxially entering the camera 21 along its optical axis L pass through the moving lens 54 as a component of a focusing mechanism, and reach the wavelength selection filter 53. The visible light that has entered coaxially together with the fluorescence is reflected by the wavelength selection filter 53, and enters the visible light image sensor 51. The fluorescence that has entered coaxially together with the visible light passes through the wavelength selection filter 53, and enters the fluorescence image sensor 52. At this time, by the action of the focusing mechanism including the moving lens 54, the visible light is focused on the visible light image sensor 51, while the fluorescence is focused on the fluorescence image sensor 52.

Figure 6:
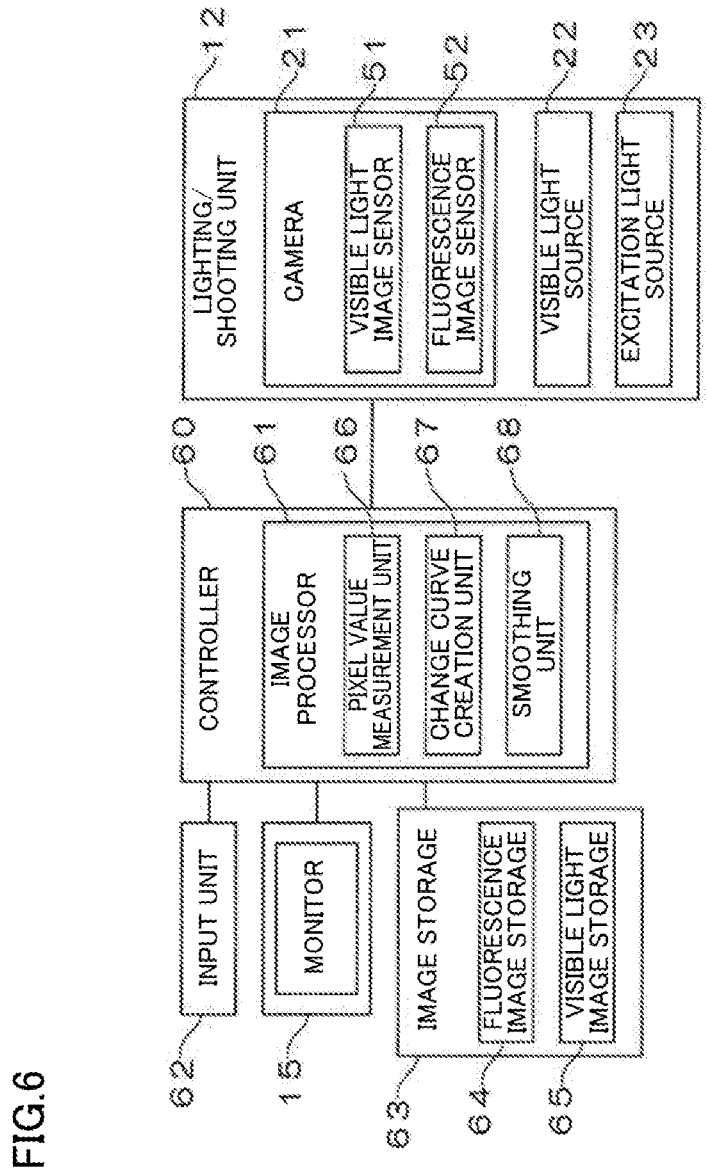
FIG. 6 is a block diagram illustrating a major control system of the imaging device of the present disclosure.

FIG. 6 is a block diagram illustrating a major control system of the imaging device of the present disclosure.

The imaging device includes a controller 60 comprised of a CPU which executes logical operations, a ROM which stores programs necessary for controlling the device, and a RAM which temporarily stores data during control. The controller 60 entirely controls the imaging device. The controller 60 includes an image processor 61 which executes various types of image processing on fluorescence images and visible light images. The image processor 61 includes a pixel value measurement unit 66, a change curve creation unit 67, and a smoothing unit 68, as will be described later. The pixel value measurement unit 66 sequentially measures values of pixels at positions corresponding to a region of interest (ROI) in a fluorescence image. The change curve creation unit 67 creates a curve of time-varying changes in pixel value of the ROI by sampling, among the pixel values measured by the pixel value measurement unit 66, the maximum pixel value within a period equal to longer than the cycle of a body motion of a subject. The smoothing unit 68 smooths the curve created by the change curve creation unit 67.

The controller 60 is connected to an input unit 62 through which an operator enters various information items. The controller 60 is connected to the monitor 15. The input unit 62 may be provided for a remote control used to operate the imaging device from a distance. If the monitor 15 is a touch panel, the input unit 62 may be shown on a screen of the monitor 15, or disposed on the wagon 11.

Further, the controller 60 is connected to the lighting/shooting unit 12 including the camera 21, the visible light source 22, and the excitation light source 23. The controller 60 is also connected to an image storage 63 which sequentially stores images taken by the camera 21. The image storage 63 includes a fluorescence image storage 64 which sequentially stores fluorescence images, and a visible light image storage 65 which sequentially stores visible light images. The fluorescence image storage 64 and the visible light image storage 65 may be replaced with a synthetic image storage which sequentially stores images obtained by synthesis (fusion) of the visible light images and the fluorescence images.

Figure 7:
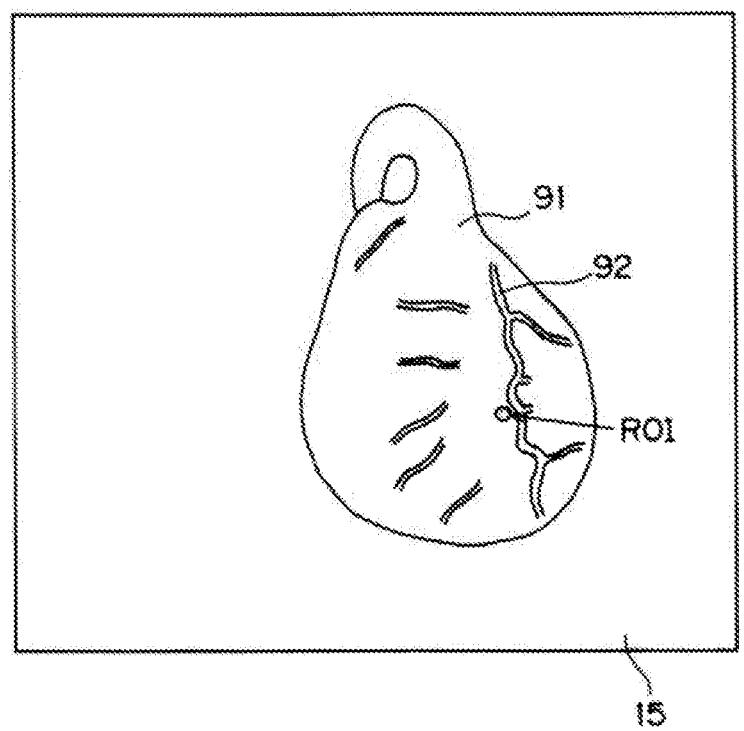
FIG. 7 is a schematic view illustrating an image of a region of a heart 91 shown on a monitor 15.

It will be described below an imaging operation using the imaging device configured as described above. For example, it will be described below the case where a TIC analysis is performed to obtain a curve of time-varying changes in pixel value of the ROI in a fluorescence image for the purpose of confirmation of blood flow after coronary artery bypass graft surgery. FIG. 7 is a schematic view illustrating an image of a region of a heart 91 shown on the monitor 15.

In this embodiment, a portion of a myocardial region of the heart 91 adjacent to a cardiac vessel 92 is selected as the ROI, and time-varying changes in pixel value of the ROI in a fluorescence image are measured. When the myocardial region is the ROI, a TIC analysis performed through observation of the time-varying changes in pixel value of the ROI in a fluorescence image is effective in confirming the blood flow after coronary artery bypass graft surgery. On the other hand, if a portion of the myocardial region adjacent to the cardiac vessel 92 is selected as the ROI for the analysis, the cardiac vessel 92 moving with the pulsation enters a region of pixel value measurement. As a result, periodical components of an image of the cardiac muscle region associated with the subject's body motion are superimposed on the TIC. Therefore, according to the imaging device of the present disclosure, among values of pixels at positions corresponding to the ROI in a fluorescence image taken by the camera 21, the minimum pixel value within a period equal to or longer than the cycle of the subject's body motion, i.e., his or her pulsation, is sampled.

Figure 8:
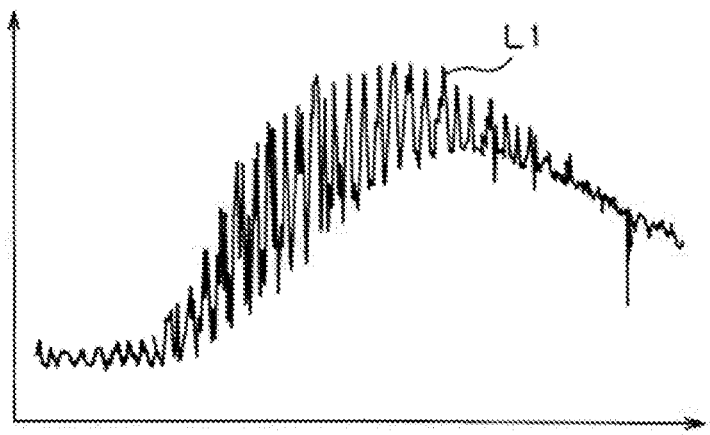
FIG. 8 is a graph of pixel values of a region corresponding to a ROI in an image of a subject taken by a camera 21.
Figure 9:
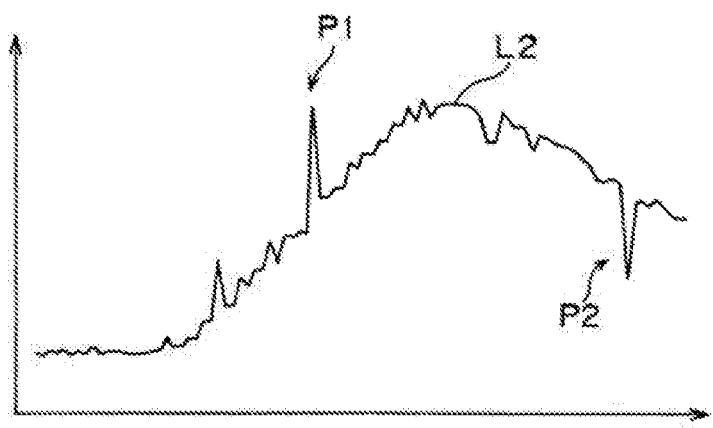
FIG. 9 is a graph obtained through sampling of the graph of FIG. 8.
Figure 10:
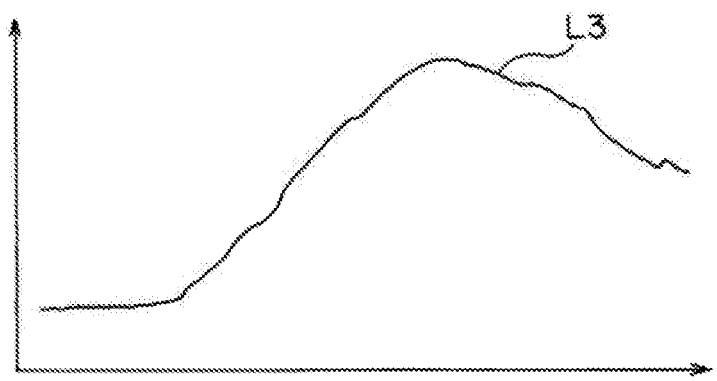
FIG. 10 is a graph obtained through smoothing of the graph of FIG. 9.

FIG. 8 is a graph of pixel values of a region corresponding to the ROI in an image of a subject taken by the camera 21. FIG. 9 is a graph obtained through sampling of the graph of FIG. 8. FIG. 10 is a graph obtained through smoothing of the graph of FIG. 9. In these graphs, a vertical axis represents the pixel value, and a horizontal axis time.

In the case where the portion of the myocardial region adjacent to the cardiac vessel 92 is selected as the ROI and the time-varying changes in pixel value of the ROI in a fluorescence image are measured, the pixel value measurement unit 66 shown in FIG. 6 measures pixel values of a region corresponding to the ROI in a fluorescence image captured by the fluorescence image sensor 52 of the camera 21. In this context, the "region corresponding to the ROI" is a region corresponding to the position of the ROI when the subject makes no body motion. The TIC analysis requires sequential measurement of the pixel values of the ROI. Actually, the position of the ROI changes with the pulsation of the subject. Therefore, in this embodiment, a region where the ROI is present when the subject makes no body motion is regarded as the region corresponding to the ROI, and the pixel values of this region are measured.

The measurement of the pixel values of the region corresponding to the ROI are continuously performed for a certain period, and the pixel values of the region corresponding to the ROI obtained in this period in every image are displayed as a curve L1 shown in FIG. 8. For example, if the pixel value measurement is performed for 30 seconds at a frame rate of 60 fps (frame per second), 1800 pixel values are measured.

In such a case, as shown in FIG. 8, the curve L1 of the pixel values of the region corresponding to the ROI repeatedly rises and falls at intervals equivalent to the pulsation cycle. This is because the position of the ROI changes with the pulsation of the subject and the cardiac vessel 92 enters the region corresponding to the ROI.

Therefore, according to the imaging device of the present disclosure, the change curve creation unit 67 shown in FIG. 6 samples, among the pixel values measured by the pixel value measurement unit 66, the minimum pixel value within a period equal to or longer than the cycle of the subject's body motion caused by his or her pulsation. Specifically, among the pixel values varying in a single cycle of the subject's body motion caused by the pulsation, the lowest pixel value is extracted. Then, the changes in the extracted pixel value are plotted as a graph. FIG. 9 shows a curve L2 of the changes in pixel value obtained by sampling the minimum pixel value.

Since the curve L2 is obtained by sampling the minimum pixel value within the period equal to or longer than the cycle of the subject's body motion caused by his or her pulsation, influence of the entry of the cardiac vessel 92 due to the pulsation of the subject can be eliminated. Thus, the curve L2 corresponds to a curve of time-varying changes in pixel value of the ROI.

The curve L2 shown in FIG. 9 has two peaks P1 and P2. Of the peaks P1 and P2, the peak P1 indicates, for example, a state where the subject's pulsation was irregular, and the cardiac vessel 92 was present at all times in the region corresponding to the ROI during the period equal to or longer than the cycle of the subject's body motion caused by his or her pulsation. The peak P2 indicates, for example, a state where a tool such as a surgical knife entered the region corresponding to the ROI.

Then, the smoothing unit 68 shown in FIG. 6 smooths the curve L2 of FIG. 9 corresponding to the curve of time-varying changes in pixel value of the ROI. As a result, the peaks P1 and P2 are excluded as shown in FIG. 10, and a curve L3, which is a curve of time-varying changes in pixel value of the ROI, can be obtained.

The "period equal to or longer than the cycle of the subject's body motion caused by his or her pulsation" is, for example, a period slightly longer than the cycle of the subject's body motion. For example, if the heart of the subject beat every second (60 times per minute), the period would be equal to or longer than one second. Setting the period longer makes it possible to obtain a curve of time-varying changes in pixel value of the ROI, which is smoothed and has no unwanted peaks, even if the smoothing described above is omitted. Therefore, in such a case, the smoothing described above can be omitted. However, setting the period longer causes a time lag in the curve of time-varying changes in pixel value of the ROI. Therefore, in a preferred embodiment, the "period equal to or longer than the cycle of the subject's body motion caused by his or her pulsation" is longer than, and shorter than the twice of, the cycle of the subject's body motion. In other words, in a preferred embodiment, the "period equal to or longer than the cycle of the subject's body motion caused by his or her pulsation" is longer than a single cycle, and shorter than two cycles, of the subject's body motion.

It has been described in the foregoing embodiment that indocyanine green is used as the fluorescent dye, and irradiated with near-infrared light of about 600 to 850 nm as the excitation light so that fluorescence in a near-infrared region having a peak around 810 nm is emitted from indocyanine green. Alternatively, light other than the near-infrared light may be used.

Further, indocyanine green used as the fluorescent dye may be replaced with other fluorescent dye such as 5-ALA mentioned above.

What is claimed is:

1. An imaging device comprising: an excitation light source which irradiates a subject with excitation light for exciting a fluorescent dye administered to the subject;
    an imaging sensor configured to obtain a fluorescence image by detecting fluorescence emitted from the fluorescent dye irradiated with the excitation light; and
    an image storage which sequentially stores the fluorescence image that changes with a body motion of a subject;
    the imaging device further comprising a controller with an image processor which includes: a pixel value measurement unit which sequentially measures values of pixels at positions corresponding to a region of interest in the fluorescence image; and
    a change curve creation unit which creates a curve of time-varying changes in pixel value of the region of interest by sampling, among the pixel values measured by the pixel value measurement unit, a maximum pixel value within a period equal to or longer than a cycle of the subject's body motion.

2. The imaging device of claim 1, the image processor further comprising:
    a smoothing unit which smooths excludes one or more peaks of the curve created by the change curve creation unit.

\* \* \* \* \*